United States Patent
Elias et al.

(10) Patent No.: US 6,562,606 B1
(45) Date of Patent: *May 13, 2003

(54) METHODS AND COMPOSITIONS FOR DISRUPTING THE EPITHELIAL BARRIER FUNCTION

(75) Inventors: Peter M. Elias, Muir Beach, CA (US); Kenneth R. Feingold, Saan Rafael, CA (US); Walter M. Holleran, San Francisco, CA (US)

(73) Assignees: The Regents of the University of California, Oakland, CA (US); Cellegy Pharmaceuticals, Inc., Foster City, CA (US)

( * ) Notice: Subject to any disclaimer, the term of this patent is extended or adjusted under 35 U.S.C. 154(b) by 98 days.

This patent is subject to a terminal disclaimer.

(21) Appl. No.: 09/608,568

(22) Filed: Jun. 30, 2000

Related U.S. Application Data

(63) Continuation of application No. 09/058,401, filed on Apr. 9, 1998, now Pat. No. 6,190,894, which is a continuation of application No. 08/733,712, filed on Oct. 23, 1996, now abandoned, which is a continuation-in-part of application No. 08/260,559, filed on Jun. 16, 1994, now abandoned, which is a continuation-in-part of application No. 08/033,811, filed on Mar. 19, 1993, now abandoned.

(51) Int. Cl.$^7$ ................................. C12N 9/00
(52) U.S. Cl. ..................... 435/183; 435/184; 435/193; 435/208; 435/232; 424/94.1; 424/94.5; 514/946; 514/947
(58) Field of Search ................. 435/183, 184, 435/193, 208, 232; 424/94.1, 94.5; 514/946, 947

(56) References Cited

U.S. PATENT DOCUMENTS

| | | |
|---|---|---|
| 4,420,474 A | 12/1983 | Sykes |
| 4,946,670 A | 8/1990 | Sebag et al. |
| 5,120,545 A | 6/1992 | Ledger et al. |
| 5,130,139 A | 7/1992 | Cormier et al. |
| 6,190,894 B1 * | 2/2001 | Thornfeldt et al. |

FOREIGN PATENT DOCUMENTS

| | | |
|---|---|---|
| DE | 3325506 A1 | 1/1985 |
| GB | 1051461 A | 12/1966 |
| GB | 1070593 A | 6/1967 |
| JP | 03153634 A | 1/1991 |

OTHER PUBLICATIONS

American Pharmaceutical Association, "Handbook of Pharmaceutical Excipients", *American Pharmaceutical Association (Washington D.C.)*, pp. 1242–1243.

Budavari, et al. "The Merck Index" *published by Merck & Co., Inc.* (New Jersey), p. 208.

Fransson, et al. "Effects of Cycloheximide, Brefeldin A, Suramin, Heparin and Primaquine on Proteoglycan and Glycosaminoglycan Biosynthesis in Human Embryonic Skin Fibroblasts" *Biochimica et Biophysica Acta* (1992) vol. 1137, pp. 287–297.

Gennaro, et al. "Remington's Pharmaceutical Sciences" *published by Mack (Pennsylvania)*, pp. 1242–1243.

* cited by examiner

*Primary Examiner*—Leon B. Lankford, Jr.
(74) *Attorney, Agent, or Firm*—Townsend and Townsend and Crew LLP

(57) ABSTRACT

A method for disrupting epithelial barrier function in a host in need of the topical administration of a physiologically active substance which comprises applying to the epithelium of the host, barrier-disrupting amount of at least one agent selected from the group consisting of an inhibitor of ceramide synthesis, inhibitor of acylceramide synthesis, inhibitor of glucosylceramide synthesis, and inhibitor of sphingomyelin synthesis, an inhibitor of fatty acid synthesis, an inhibitor of cholesterol synthesis, a degradation enzyme of ceramides, acylceramide, glucosylceramides, sphingomyelin, an inhibitor of phospholipid, glycosphingolipid, including glucosylceramide, acylceramide or sphingomyelin degradation, and both inhibitors and stimulators of metabolic enzymes of free fatty acids, ceramide, and cholesterol, as well as a topical composition useful therefor are disclosed.

23 Claims, 5 Drawing Sheets

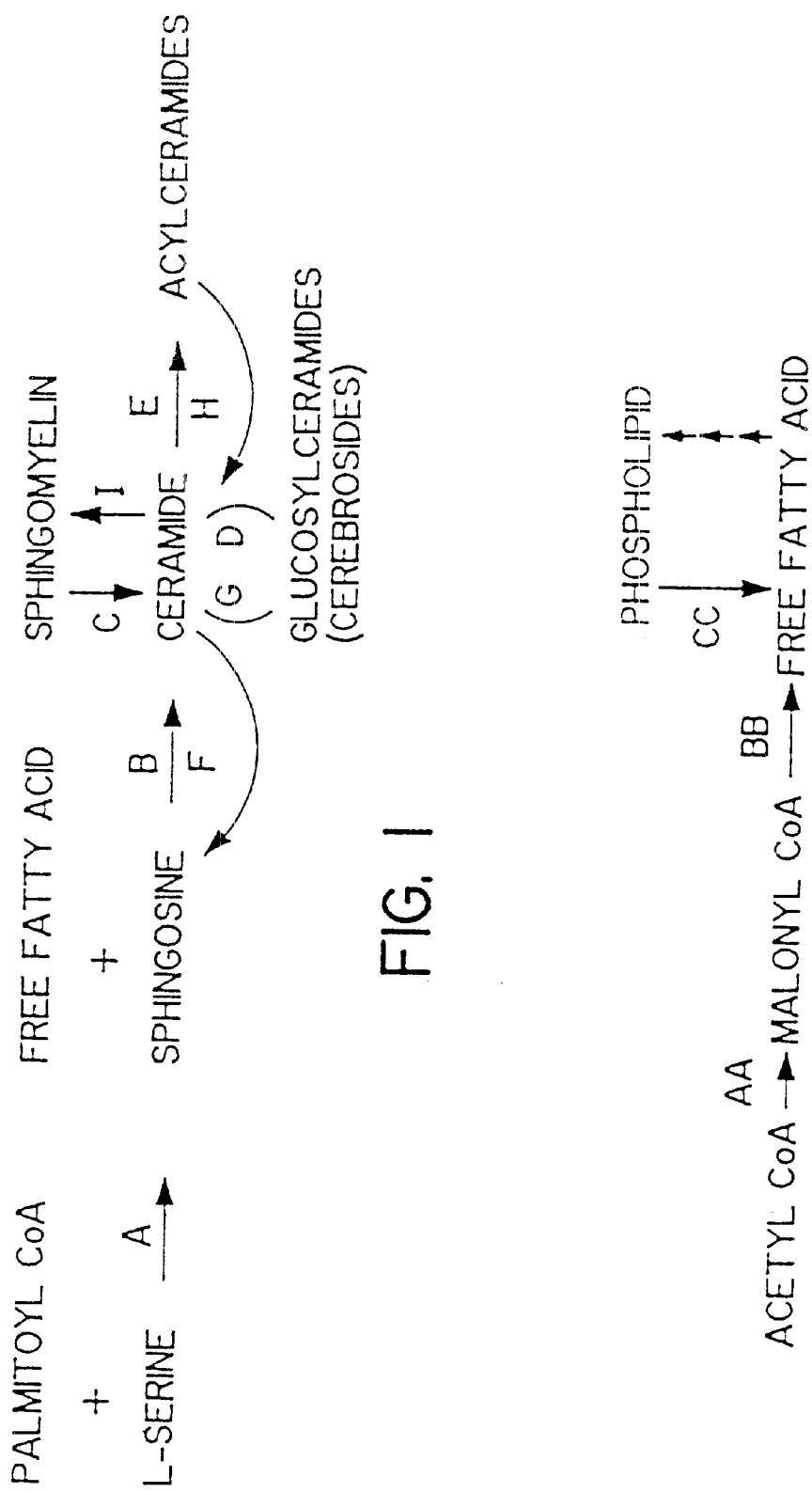

METHODS AND COMPOSITIONS FOR DISRUPTING THE EPITHELIAL BARRIER FUNCTION

This application is a continuation of application Ser. No. 09/058,401, filed Apr. 9, 1998, U.S. Pat. No. 6,190,894, which is a conitinuation of application Ser. No. 08/733,712, filed Oct. 23, 1996, now abandoned, which is a continuation-in-part of application Ser. No. 08/260,559, filed Jun. 16, 1994, now abandoned, which is a continuation-in-part of application Ser. No. 08/033,811, filed Mar. 19, 1993, now abandoned. All of the applications cited in this paragraph are incorporated herein by reference.

GOVERNMENT RIGHTS

This invention was made with Government support by The Department of Veterans Affairs. The Government may therefore have certain rights in this invention.

BACKGROUND OF THE INVENTION

1. Field of the Invention

This invention relates generally to a novel method for enhancing penetration of physiologically active substances for cutaneous or transdermal delivery through epithelium which comprises the stratum corneum/epidermis and keratinizing mucous membranes. More specifically, it relates to a method and composition for disrupting the epithelial barrier function in a host which employs at least one agent selected from the group consisting of inhibitors of ceramide synthesis, an inhibitor of glucosylceramide synthesis, an inhibitor of acylceramide synthesis, an inhibitor of sphingomyelin synthesis, an inhibitor of fatty acid synthesis, an inhibitor of cholesterol synthesis, inhibitors of phospholipid, glycosphingolipid, including glucosylceramide, acylceramide and sphingomyelin degradation, a degradation enzyme of free fatty acid, ceramide, acylceramide, or glucosylceramides and sphingomyelin, and both inhibitors and stimulators of metabolic enzymes of free fatty acids, ceramide, and cholesterol.

2. Description of Related Art

The major function of the epithelium is that of a barrier to prevent the excessive loss of bodily fluids. If this barrier is disrupted or perturbed, it stimulates a variety of metabolic changes in the epithelium leading to repair of the barrier defect. While the barrier protects against external damage induced by such agents as ultraviolet radiation, desiccation, chemicals, and frictional or blunt trauma, it impedes the penetration of topically applied medicaments, nutrients, or other xenobiotics.

The epithelial barrier is a system of multilayered membrane lipid bilayers that exist throughout the intercellular spaces of the stratum corneum in epidermis and keratinizing mucous membranes. The bilayers in stratum corneum of epidermis consist of approximately equimolar ratios of three major lipid species: ceramides, free fatty acids, and cholesterol, as well as small, but critical, amounts of acylceramides. Keratinizing mucous membrane multilayered bilayers consist of approximately equimolar ratios of glucosylceramides, free fatty acids and cholesterol. These lipid species are synthesized in the subjacent nucleated cell layers of the epithelium. Following any type of barrier perturbation, an increase in lipid biosynthesis occurs, which leads to the recovery of barrier structure and function. The more extensive the perturbation of the barrier, the more active is the subsequent lipid biosynthetic response.

In addition to the long-standing approaches of hydration and occlusion, currently available percutaneous and transmucosal penetration enhancement technology relies on physical-chemical methods, such as solvents or detergents, and physical approaches, such as iontophoresis, electroporation, or sonophoresis. Typical solvents or detergents alter the physical properties of the multilayered lipid bilayers. Such agents include dimethylsulfoxide (DMSO), oleyl alcohol (OA), propylene glycol (PG), methyl pyrrolidone and AZONE® (dodecylazyl cycloheptan 2-one). For example, U.S. Pat. No. 4,177,267 discloses topical steroid compositions containing dimethylsulfoxide as an epithelial penetration enhancer. It is generally believed that many of these epithelial penetration enhancers fluidize the polar head group (e.g., DMSO) and/or nonpolar tail group (e.g., OA) domains within the multilayered lipid bilayers. Yet, some compounds with significant fluidizing effect have been shown to be incapable of substantially increasing epithelial permeability. While these methods enhance penetration of certain compounds by three- to five-fold, these methods are only relatively effective for smaller lipophilic and amphiphathic molecules. Hydrophilic compounds such as proteins or peptides do not penetrate in pharmaceutically useful quantities through the epithelia even when most of these permeation technologies are utilized.

Accordingly, there is a need for epithelial penetration enhancers capable of allowing and/or increasing the penetration of large and/or water-soluble molecules in therapeutically effective quantities. This invention addresses this need by providing methods and topical compositions for disrupting the epithelial barrier thereby facilitating the penetration of therapeutic known or potential molecules.

SUMMARY OF THE INVENTION

It has been discovered that a formulation comprising at least one agent selected from the group consisting of inhibitors of ceramide synthesis, inhibitors of glucosylceramide synthesis, inhibitors of acylceramide synthesis, inhibitors of fatty acid synthesis, inhibitors of cholesterol synthesis, and inhibitors of phospholipid, glycosphingolipid, acylceramide or sphingomyelin degradation, is very effective for disrupting epithelial barrier function in a host, and thereby enhancing penetration of a physiologically active substance administered topically.

In one aspect thereof, this invention provides a method for disrupting epithelial barrier function in a host in need of topical administration of a physiologically active substance which comprises applying to the skin of the host a barrier-disrupting amount of at least one agent selected from the group consisting of inhibitors of ceramide synthesis, inhibitors of acylceramide synthesis, inhibitors of glucosylceramide synthesis, inhibitors of free fatty acid synthesis, inhibitors of cholesterol synthesis, inhibitors of degradation of a phospholipid, glycosphingolipid, acylceramide or sphingomyelin, both inhibitors and a stimulators of steps of free fatty acid ceramide and cholesterol metabolism distal to these compounds, and degradation enzymes of free fatty acids, ceramides, acylceramides, or glucosylceramides and sphingomyelin, and both inhibitors and stimulators of metabolic enzymes of free fatty acids, ceramide, and cholesterol.

In another aspect, this invention provides a topical composition for disrupting epithelial barrier function in a host in need of topical administration of a physiologically active substance which comprises an epithelial barrier-disrupting amount of at least one agent selected from the group consisting of an inhibitor of ceramide synthesis, an inhibitor of acylceramide synthesis, an inhibitor of glucosylceramide synthesis, an inhibitor of sphingomyelin synthesis, an inhibitor of free fatty acid synthesis, and an inhibitor of cholesterol synthesis, inhibitors of phospholipid, glycosphingolipid, including glycosylceramide, acylceramide and sphingomyelin degradation, a degradation enzyme of free fatty acid, ceramide, acylceramide, sphingomyelin or glucosylceramides and both inhibitors and stimulators of metabolic enzymes of free fatty acids, ceramide, and cholesterol The above features and advantages of this invention will be more fully understood by reference to the following detailed description and the drawings.

BRIEF DESCRIPTION OF THE DRAWINGS

FIG. 1 schematically shows a biosynthetic and degradation pathway of ceramides, acylceramides and glucosylceramides.

FIG. 2 schematically shows a biosynthetic pathway of free fatty acids.

DETAILED DESCRIPTION OF THE INVENTION

Figure 3:
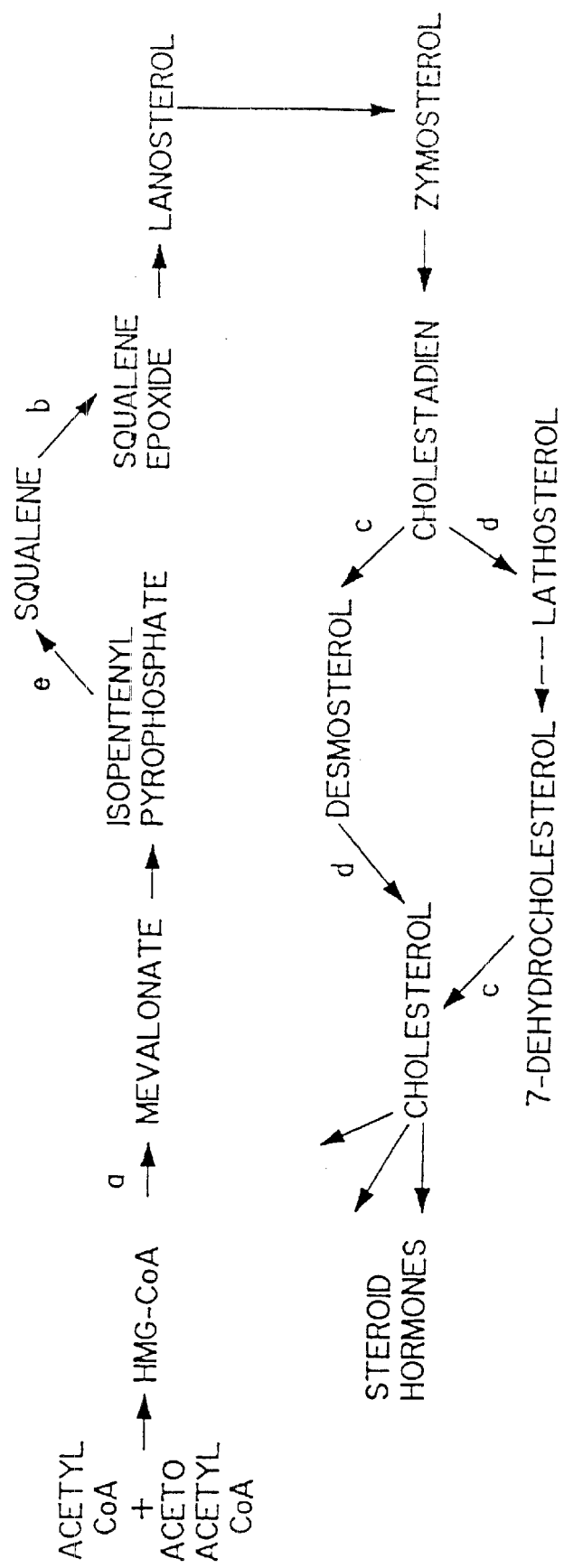
FIG. 3 schematically shows a biosynthetic and degradation pathway of cholesterol.

This invention is based on the discovery that when the biosynthesis of one or more of the epithelial lipids, ceramides, acylceramide, glucosylceramides, sphingomyelin, cholesterol and free fatty acids is inhibited, or their distal utilization is increased, the lipid species is depleted perturbing the normal mole ratio, resulting in incompetent epithelial barrier function. Inhibition of enzymes involved in a biosynthetic pathway or inhibition of the degradation enzymes for the precursors of each of these key lipid constituents have also been specifically targeted according to the present invention. Further, it has been discovered that the inhibition of biosynthetic enzymes or stimulation of degradative enzymes aiming at two or more lipid constituents may be additive or synergistic in the opening of the epithelial barrier for percutaneous or transmucosal delivery of physiologically active substances.

The composition of this invention principally employs an epithelial barrier-disrupting amount of at least one agent selected from the group consisting of inhibitors of ceramide synthesis, an inhibitor of sphingomyelin synthesis, an inhibitor of glucosylceramide synthesis, an inhibitor of acylceramide synthesis, an inhibitor of sphingomyelin synthesis, an inhibitor of fatty acid synthesis, an inhibitor of cholesterol synthesis, inhibitors of phospholipid, glycosphingolipid, including glucosylceramide, acylceramide and sphingomyelin degradation, a degradation enzyme of free fatty acid, ceramide, acylceramide, or glucosylceramides and sphingomyelin and both inhibitors and stimulators of metabolic enzymes of free fatty acids, ceramide, and cholesterol.

As used herein, the term "an epithelial barrier-disrupting amount" means that the amount of enzyme inhibitor(s), stimulator(s) or degradation enzymes are of sufficient quantity to disrupt the barrier when these compounds are topically applied to the skin or mucous membrane of a host. The amount can vary according to the effectiveness of each enzyme inhibitor or stimulator, or degradation enzyme, as a percutaneous or transmucosal penetration enhancer, the host age, and response of the host. More importantly, the therapeutic amount should be determined based on the penetration efficiency of a given physiologically active substance when that substance is administered in conjunction with a particular combination of the enzyme inhibitors or stimulators, or degradation enzymes. The required quantity to be employed in this invention can be determined readily by those skilled in the art.

As used herein, the term "host" includes humans and non-human mammals. Non-human mammals of particular interest are domesticated species such as dogs, cats, monkeys, cows, horses, llamas, sheep, pigs, and goats.

The term "penetration enhancement" or "permeation enhancement" as used herein relates to an increase in the permeability of skin to a physiologically active substance, i.e., so as to increase the rate at which the substance permeates through the epithelium and enters the bloodstream.

As applied in this invention, the term "physiologically active substance" is intended to encompass any substance that will produce a physiological response when topically administered to a host. In general, the terms include therapeutic or prophylactic agents in all major therapeutic/prophylactic areas of medicine as well as nutrients, cofactors, enzymes (endogenous or foreign), antioxidants or other defensive principals, and xenobiotics. Suitable substances include, but are not restricted to, antifungals such as amphotericin B, griseofulvin, miconazole, ketoconazole, tioconazol, itraconazole, and fluconazole; antibacterials such as penicillins, cephalosporins, tetracyclines, aminoglucosides, erythromycin, gentamicins, polymyxin B; anti-cancer agents such as 5-fluorouracil, bleomycin, methotrexate, hydroxyurea; anti-inflammatories such as hydrocortisone, glucocorticoids, colchicine, ibuprofen, indomethacin, and piroxicam; antioxidants, such as tocopherols, retinoids, carotenoids, ubiquinones, metal chelators, and phytic acid; antihypertensive agents such as prazosin, verapamil, nifedipine, and diltiazem; analgesics such as acetaminophen and aspirin; anti-viral agents such as acyclovir, ribavarin, and triflucrothyridine; antiandrogens such as spironolactone; androgens such as testosterone; estrogens such as estradiol; progestins such as modified progestogens; opiates; muscle relaxants such as papaverine; vasodilators such as nitroglycerin, vasoactive intestinal peptide and calcitonin related gene peptide; antihistamines such as cyproheptadine; agents with histamine receptor site blocking such as doxepin, imipramine, and cimetidine; antitussives such as dextromethorphan; neuroleptics such as clozaril; antiarrhythmics; antiepileptics; and other polypeptides and neuropeptides such as somatostatin, various cytokines, insulin, gastrin, substance P, and capsaicin; and enzymes, such as superoxide dismutase and neuroenkephalinase. Other useful drugs, in approved commercially available formulations, and their recommended dosages are listed in the annual publication of the Physicians' Desk Reference, published by Medical Economics Company, a division of Litton Industries, Inc. More than one physiologically active substance may be included, if desired, in the topical composition of this invention.

The active substance may be water-soluble or water-insoluble and may include higher molecular weight proteins, peptides, carbohydrates, glycoproteins, lipids, and glycolipids. Such proteinaceous active substances which can be included are immunomodulators and other biological response modifiers. Examples of immune response modifiers include such compounds as cytokines, including tumor necrosis factors, interleukins, growth factors, colony stimulating factors, and interferons.

The active substance will be present in the composition in an amount sufficient to provide the desired physiological effect with no apparent toxicity to the host. Of course, the appropriate dosage levels of all the physiologically active substances, without the use of the epithelial barrier-disrupting agents of the present invention, are known to one skilled in the art. These conventional dosage levels correspond to the upper range of dosage levels for compositions, including a physiologically active substance and an epithelial barrier-disrupting agent. However, because the delivery of the active substance is enhanced by the epithelial barrier-disrupting agent of this invention, dosage levels significantly lowering the conventional dosage levels may be used with success. In general, the active substance will be present in the composition in an amount of from about 0.0001% to about 60%, more preferably about 0.01% to about 20% by weight of the total composition depending upon the particular substance employed.

Ceramides, including acylceramides, account for 40–50% by weight of the stratum corneum lipids while glucosylceramides account for a similar percent in mucosal membranes. Representative in vivo biosynthetic pathways for these lipid species are shown in FIG. 1. Among many enzymes involved in these biosynthetic pathways, serine palmitoyl transferase is the rate limiting enzyme.

The inhibitors of ceramide, acylceramide, sphingomyelin, and glucosylceramide synthesis and metabolism include inhibitors of serine palmitoyl transferase such as β-chloroalanine, fluoropalmitate, and β-fluoroalanine, and inhibitors of ceramide synthetase such as chloroquine, gramicidin D, fumonisins. Inhibitors of sphingomyelinase include agents such as tricyclodecan-9-yl-xanthogenate, ethylisopropylamiloride, N-palmitoyl-DL-dihydrosphingosine, methylene-dioxybenzapine, tricyclodecan-9yi-xanthogenate; aminoglycosides including gentamicin and neomycin; ethyliso-proplylamiloride; tricyclic antidepressants, including desipramine and imipramine; and phenothiazines including chlorpromazine and perchlorperazine. Inhibitors of glucosylceramide synthesis further include inhibitors of UDP-glucose-ceramide glucosyl transferase (glucosyl transferase), such as 1-phenyl-2-deanoylamino-3-morphalino-1-propanol (PDMP), its analogs, α- and β-xylosides; and alpha xylosides including p-nitro-phenyl-α-xyloside and beta xylosides including 4-methyl umbelliferyl-β-0-xyloside, 0-and p-nitrophenyl-β-0-xylopyaranoside. Inhibitors of acylceramide synthesis further include inhibitors of α-hydroxylation, N-acyl chain length elongation, and ω-acyl transferase. Inhibitors of acid lipase include the boronic acids, including phenylboronic acid, tetrahydrolipstatin and esterasin.

In keratinizing mucous membrane, glycosphingolipids, including glucosylceramide, are not metabolized into ceramide, as occurs in the stratum corneum. Therefore, inhibitors of glycosphingolipids including inhibitors of β-glucosidase such as N-hexylglucosyl-sphingosine, bromoconduritol B-epoxide, conduritol, cyclophellitol, conduritol B-epoxide, and deoxynojirimycin will effectively perturb the barrier in the stratum corneum, but not in the keratinized mucous membranes. D-cycloserine, β-chloroalanine, L-cycloserine, β-fluoroalanine, fluoropalmitate, and fumonisins are preferred inhibitors of epithelial sphingolipid synthesis, with β-chloroalanine and fumonisins being most preferred. Stimulators of glucosyl transferase, α-hydroxylation, N-acyl chain length elongation, and ω-acyl transferase and phosphotidylcholine-ceramide phosphorylcholine transferase will effect epithelial ceramide and glucosylceramide concentrations. An effective concentration range for these inhibitors and stimulators in the topical composition of this invention is generally from about 0.0001% to about 20% by weight of the total, with about 0.01% to about 5% preferred.

Free fatty acids account for 20–25% of the epithelial lipids by weight. The free fatty acids are synthesized and metabolized in vivo as shown in FIG. 2. The two rate limiting enzymes in the biosynthesis of the free fatty acids are acetyl CoA carboxylase and fatty acid synthetase. Through a series of steps, free fatty acids are metabolized into phospholipids.

The inhibitors of free fatty acid synthesis and metabolism include inhibitors of acetyl CoA carboxylase such as 5-tetradecyloxy-2-furancarboxylic acid (TOFA); inhibitors of fatty acid synthetase; inhibitors of phospholipase A such as gomisin A, 2-(p-amylcinnamyl)amino-4-chlorobenzoic acid, bromophenacyl bromide, monoalide, 7,7-dimethyl-5,8-eicosadienoic acid, nicergoline, cepharanthine, nicardipine, quercetin, dibutyryl-cyclic AMP, R-24571, N-oleoylethanolamine, N-(7-nitro-2,1,3-benzoxadiazol-4-yl) phosphostidyl serine, cyclosporine A, topical anesthetics, including dibucaine, prenylamine, retinoids, such as all-trans and 13-cis-retinoic acid, W-7, trifluoperazine, R-24571 (calmidazolium), 1-hexadocyl-3-trifluoroethyl glycero-sn-2-phosphomenthol (MJ33); calcium channel blockers including nicardipine, verapamil, diltiazem, nifedipine, and nimodipine; antimalarials including quinacrine, mepacrine, chloroquine and hydroxychloroquine; beta blockers including propanalol and labetalol; calmodulin antagonists; EGTA; thimersol; glucocorticosteroids including dexamethasone and prednisolone; and nonsteroidal antiinflammatory agents including indomethacin and naproxen. Chloroquine and gramicidin D inhibit fatty acid and ceramide synthetase by inhibiting proton pumps. TOFA is the preferred inhibitor of free fatty acid synthesis. An effective concentration range for the fatty acid inhibitor in the topical composition of this invention is generally from about 0.0001% to about 20% by weight of the total, with a preferred range of about 0.01% to about 5%.

Free sterols, primarily cholesterol, account for 20–25% of the epithelial lipids by weight. The free sterols are synthesized and metabolized in vivo as shown in FIG. 3. The rate limiting enzymes in the biosynthesis of cholesterol is 3-hydroxy-3-methylglutaryl (HMG) CoA reductase.

The inhibitors of cholesterol synthesis include cornpetitive inhibitors of (HMG) CoA reductase such as simvastatin, lovastatin, fluindostatin (fluvastatin), pravastatin, mevastatin, as well as other HMG CoA reductase inhibitors, such as cholesterol oleate, cholesterol sulfate and phosphate, and oxygenated sterols, such as 25-OH- and 26-OH-cholesterol; inhibitors of squalene synthetase; inhibitors of squalene epoxidase; inhibitors of Δ7 or Δ24 reductases such as 22,25-diazacholesterol, 20,25-diazacholestenol, AY9944, and triparanol. The preferred inhibitors are fluindostatin, simvastatin, lovastatin, cholesterol sulfate, and 25-OH-cholesterol. An effective concentration range for the cholesterol inhibitor in the topical composition of this invention is generally from about 0.0001% to about 20% by weight of the total, with a preferred range of about 0.01% to about 5%.

The degradation enzyme of ceramide is ceramidase. The degradation enzymes of acylceramides are acid lipase followed by ceramidase. The degradation enzymes of glucosylceramide are β-glucocerebrosidase followed by ceramidase. The degradation enzyme of sphingomyelin is sphingomyelinase. An inhibitor of ceramidase is N-oleoyl-ethanolamine. An effective concentration range for these degradation enzymes is generally from about 0.0001% to about 20% by weight of the total, with a preferred range of about 0.01% to about 5%.

The term "stimulators of steps of ceramide, free fatty acid, and cholesterol metabolism distal to these molecules" means molecules capable of shunting cholesterol, free fatty acid or cholesterol to more distal metabolites, such as glucosylceramide, acylceramide, sphingomyelin, phospholipids; and steroid hormones, respectively. This has the effect of depleting free fatty acid, cholesterol, or ceramides. An effective concentration range for such stimulators is generally from about 0.0001% to about 20% by weight of the total, with a preferred range of about 0.01% to about 5%.

Several of the metabolic pathways mentioned herein have as yet no known inhibitors for the enzymes, such as alpha-hydroxylation, N-acyl chain length elongation, omega-acyl transferases, phosphatidylcholine-ceramide phosphorylcholine transferases, fatty acid synthetase, squalene synthetase, cholesterol phosphate synthetase, cholesterol sulfate synthetase. However, should such inhibitors be discovered, the use of such inhibitors is contemplated within the scope of this invention.

These enzyme inhibitors, degradation enzymes, or enzyme stimulators can be co-applied to the skin or mucous membrane of a host in a formulation with any combination of these compounds with or without conventional penetration enhancers or other drug delivery technology, including transderrnal patches, iontophoretic and electrophoretic devices, and sonicators. Alternatively, they can be applied concurrently as separate formulations. Still further, one agent can be applied before, simultaneously with, or after application of the other agent(s) provided that the time interval between the two (or more) is not too lengthy (e.g, typically, not more than about 24 hours). The physiologically active substance can be co-administered to the host with a topical composition which contains these inhibitors or stimulators. Alternatively, the pharmacologically active substance may be administered after application of the topical composition of the invention. It is, however, preferred to use the enzyme inhibitors or stimulators, or degradation enzymes, with the pharmacologically active compound as a single composition or formulation.

Preferably and conveniently, the combined or single inhibitor is applied to the skin in combination with a physiologically acceptable carrier. The carrier may comprise any conventional topical formulation base such as those described in Remington's "Pharmaceutical Sciences," 17th Edition (Mack Publishing Co., Pa.), the disclosure of which is incorporated by reference. A lotion, solution, cream, ointment, paste, gel, suppository, aerosol, or nebulized formulation are representative of the topical compositions of this invention.

Additional ingredients may be added to the topical composition, as long as they are physiologically acceptable and not deleterious to the epithelial cells and function. Such additives should not adversely affect the epithelial penetration efficiency of the above-noted enzyme inhibitors or stimulators, or degradation enzymes, nor cause the stability of the composition to deteriorate. Examples of ingredients which can be added to the compositions of the invention include stabilizers, preservatives, buffering agents, surfactants, emulsifiers, fragrances, humectants, and the like.

In one embodiment of this invention, a known percutaneous penetration-enhancing compound may be included in the composition to be additive or synergistic with the above enzyme inhibitors or stimulators, or degradation enzymes. Some of such penetration-enhancing compounds are described in U.S. Pat. Nos. 4,424,210 and 4,316,893, the disclosures of which. are incorporated by reference. The preferred compounds include propylene glycol, methyl pyrrolidone, oleyl alcohol, DMSO and AZONE®. The use level of the additional penetration-enhancing compounds is not significantly different from that of the enzyme inhibitors or stimulators, or degradation enzymes, and is in the range of from about 0.0001% to about 20.0% and preferably about 0.01% to about 5.0% by weight of the topical composition.

Topical lovastatin, an HMG CoA reductase inhibitor, is shown to impair the recovery of barrier function, assessed as transepidermal water loss (K. R. Feingold, et al., *J. Clin. Invest.* 88, 1338–1345, 1991). Also, β-chloro-L-alanine, an irreversible inhibitor of serine-palmitoyl-transferase, is shown to slow barrier recovery, assessed as transepidermal water loss (W. M. Holleran, et al., *J. Clin. Invest.* 88:1338, 1991). However, these references neither teach nor suggest that either compound is. capable of disrupting epidermal barrier function sufficient for percutaneous drug delivery. It is recognized by one skilled in the art that the inhibition of barrier recovery to excess water loss (inside to outside) and the disruption of epidermal barrier function sufficient for delivery of molecules much larger than water from the outside to the inside. are not correlated.

The effectiveness of the topical compositions of this invention to enhance penetration of a physiologically active substance at an epithelial site can be determined by their ability to disrupt the normal diffusion profile of marker compounds such as cyclophenol or propylene glycol through the skin.

While the present invention has been described with respect to preferred embodiments thereof, it will.be understood that various changes and modifications will be apparent to those skilled in the art and that it is intended that the invention encompass such changes and modifications as falling within the scope of the appended claims. The following non-limiting examples are provided to further illustrate the present invention.

EXAMPLE 1

The following ingredients were combined and blended uniformly together to produce a gel formulation:

| INGREDIENTS | PERCENT BY WEIGHT |
| --- | --- |
| Fluindostatin | 2.0 |
| β-chloroalanine | 1.5 |

-continued

| INGREDIENTS | PERCENT BY WEIGHT |
|---|---|
| Carboxyvinyl polymer 940 | 1.0 |
| Ethanol | 30.0 |
| Propylene glycol | 30.0 |
| Triethylamine | 1.5 |
| Distilled water | Remaining part |

A solution was prepared by mixing all the ingredients except triethylamine. Neutralization of the aqueous solution with triethylamine furnished a viscous gel.

Pharmaceutically active substances such as hydroxycortisone can be added to this gel for anti-inflammatory therapy.

EXAMPLE 2

The following ingredients were combined and blended uniformly together to produce an ointment formulation:

| INGREDIENTS | PERCENT BY WEIGHT |
|---|---|
| Fluindostatin | 1.5 |
| β-chloroalanine | 1.0 |
| Plastibase 50W (mineral oil 95%, polyethylene 5%) | Remaining part |

Blends of the active ingredients in ointment base were mixed together for 30 minutes at 40 rpm followed by 60 minutes at 25 rpm under vacuum to prevent aeration.

Pharmaceutically active substances such as erythromicin can be added to this ointment for antibacterial therapy.

EXAMPLE 3

The following ingredients were combined and blended uniformly together to produce a cream formulation:

| INGREDIENTS | PERCENT BY WEIGHT |
|---|---|
| TOFA | 1.5 |
| Fluindostatin | 1.0 |
| β-chloroalanine | 1.0 |
| Cetyl/stearyl alcohol | 25.0 |
| Glycerin | 5.0 |
| Oleic acid oleyl ester | 3.0 |
| Distilled water | Remaining part |

Cetylstearyl alcohol (25 g), 10 g of an aqueous suspension of the active ingredient and 3 g of oleic acid oleyl ester were heated to 80° C. and emulsified by stirring at that temperature with a mixture of 5 g of glycerin and 57 ml of water.

Pharmaceutically active substance such as ketoconazole can be added to this cream for antifungal therapy.

EXAMPLE 4

The following ingredients were combined and blended uniformly together to produce a cream formulation:

| INGREDIENTS | PERCENT BY WEIGHT |
|---|---|
| TOFA | 1.0 |
| Cetyl/stearyl alcohol | 40.0 |
| Polysorbate 80 | 10.0 |
| Distilled water | Remaining part |

Pharmaceutically active substance such as nifedipine can be added to this cream for ahtihypertensive therapy.

EXAMPLE 5

EPIDERMAL BARRIER DISRUPTION

To determine the epidermal barrier disruption by application of fluindostatin, an animal testing was conducted in the manner as follows:

Hairless mice (two animals, B and C) were topically pretreated with fluindostatin for 7 days. In a control group, animals (two) were only treated with a vehicle. The vehicle used was a mixture of propylene glycol (PG) and ethanol (0.5 ml of 5% w/v per deuterated PC in ethanol). The parameters for the vehicle in all of the experiments herein are as follows: TEWL 266±22 (T=4 hours); plasma concentration 0.31±0.03%; total body concentration 13.13±0.83 (% dose/ml plasma); N=14.

Figure 4A:
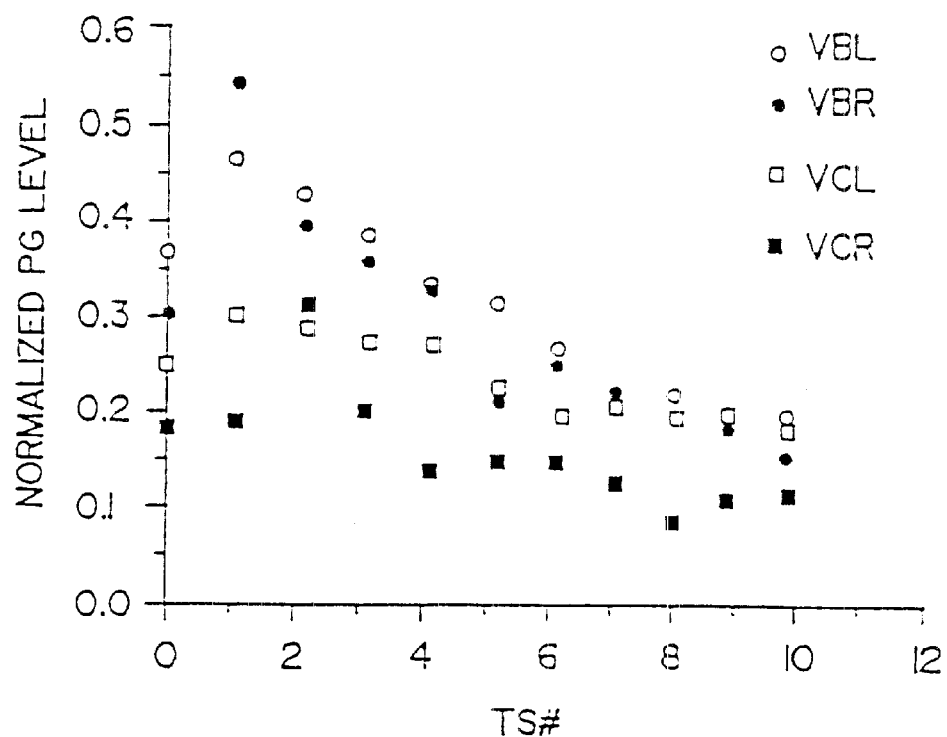
FIG. 4A shows the propylene glycol concentrations at an epidermal surface of control animals when they were treated with a vehicle. ○, VBL; ○, VBR; □, VCL; ■, VCR.
Figure 4B:
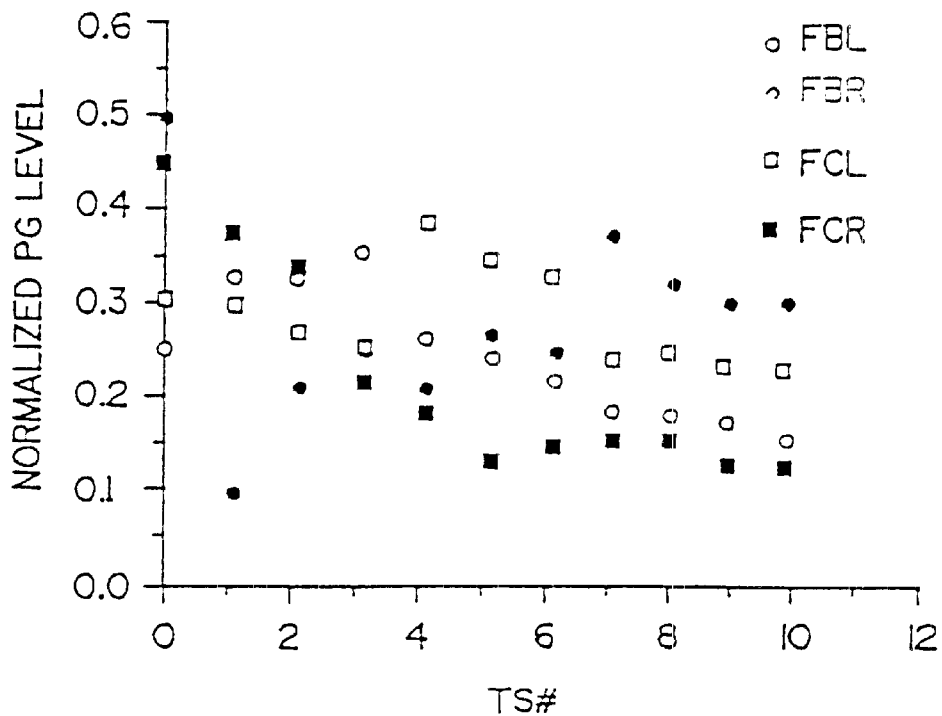
FIG. 4B shows the propylene glycol concentrations at an epiderrnal surface of tested animals when they were treated with fluvastatin (fluindostatin). ○, FBL; ○, FBR; □, FCL; ■, FCR.

After treatment, the skin surface was cleaned and stratum corneum allowed to recover to its normal state of hydration for 2 hours. An IR spectrum of the hydrophilic marker compound, propylene glycol, was recorded, and a single tape-stripping was conducted at the treated skin site. Another spectrum was recorded followed by the removal of a. second tape strip. The same sequence was repeated 10 times. FIGS. 4A, 4B show the test results. In FIG. 4A, control data indicate a gradual decrease of the PG concentration, while the data in FIG. 4B show lower absolute levels of PG in the stratum corneum, and a constant concentration level of PG, indicative of loss of the diffusional barrier to drug penetration. These results demonstrate that there is an absolute reduction of the permeability function and loss of the diffusion gradient with fluindostatin treatment, resulting in enhanced percutaneous transport of the marker compound, propylene glycol.

Figure 5A:
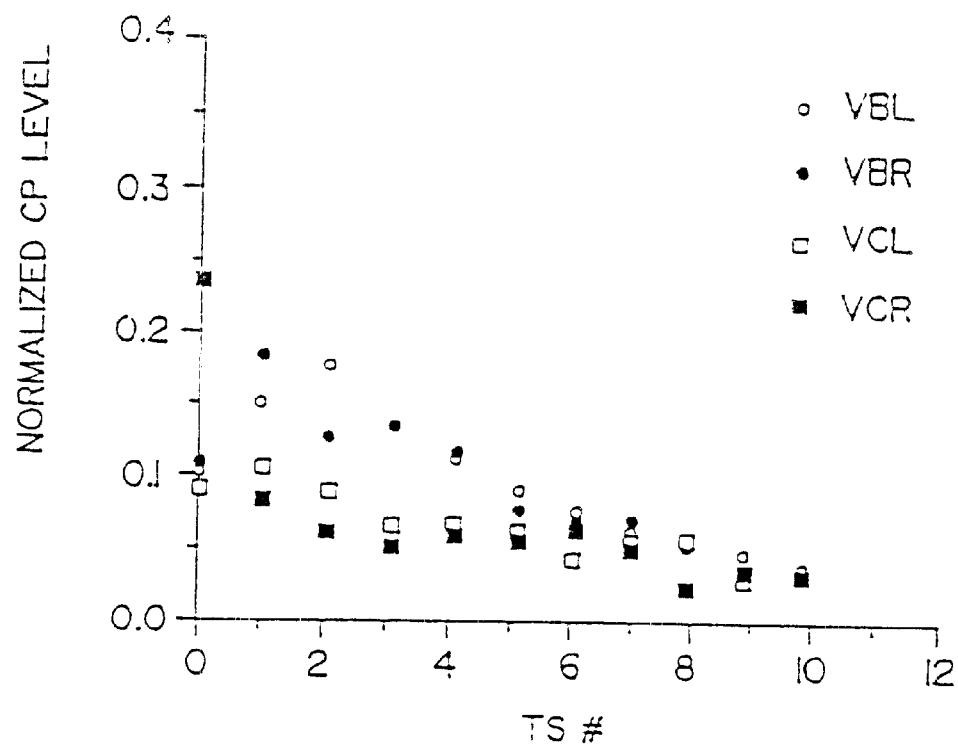
FIG. 5A shows the cyclophenol concentrations at an epidermal surface of control animals when they were treated with a vehicle. ○, VBL; ○, VBR; □,VCL; ■, VCR.
Figure 5B:
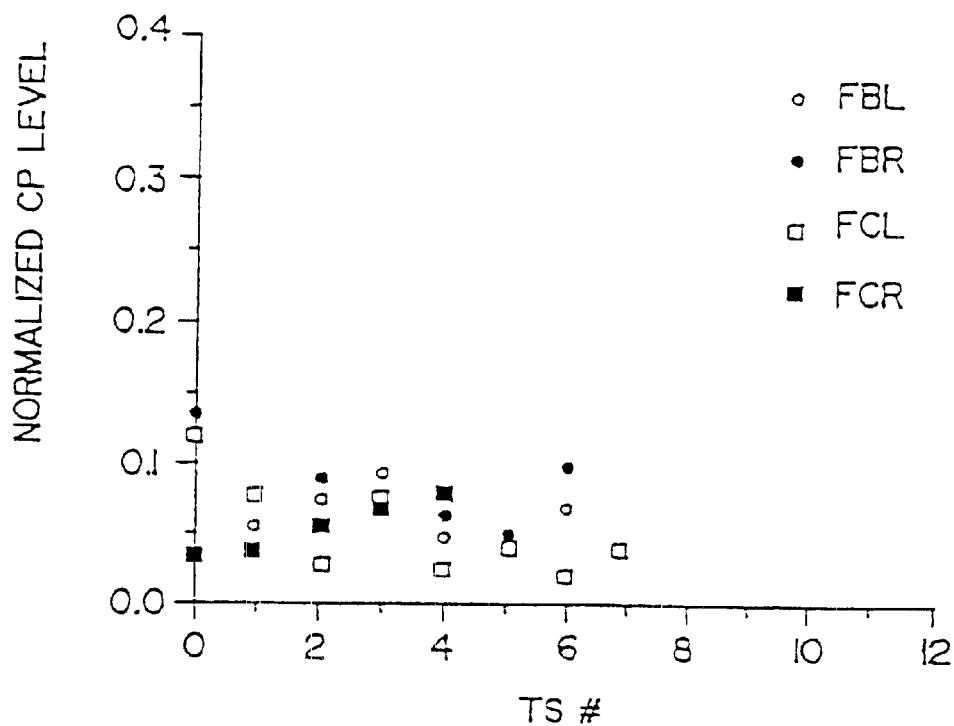
FIG. 5B shows the cyclophenol concentrations at an epidermal. surface of tested animals when they were treated with fluindostatin. ○, FBL; ○, FBR; □, FCL; ■, FCR.

In essentially the same manner, cyclophenol (CP) was used as a.lipophilic marker. Tape-stripping was repeated 7 times after application of fluindostatin. Test results are shown in FIGS. 5A, 58. In FIG. 5A, control data indicate a gradual decrease of the CP concentration, while the data in FIG. 5B show a lower, constant concentration level of CP.

Both sets of data demonstrate that fluindostatin caused significant disruption of the stratum corneum barrier, and enhanced drug delivery as illustrated both by loss of the diffusion gradient, and by the lower absolute concentrations of the marker compounds in the stratum corneum.

EXAMPLE 6

TEWL (TRANS-EPIDERMAL WATER LOSS)

A female hairless mouse, aged 8 weeks, was treated with oleic acid. After oleic acid treatment, fluindostatin and/or 5-tetradecyloxy-2-furancarboxylic acid (TOFA) was applied to the animal.

TEWL (trans-epidermal water loss) was measured before and after treatment at convenient time intervals when the animal was alert. An Evaporimeter (ServoMed) was used.

First, TEWL of the left (LHS) and right (RHS) dorsal sides was measured. Then, the animal was anesthetized by 0.25 ml chloral hydrate (CH) IP injection. At t=0, an aliquot of 30 µl oleic acid solution (5% in propylene glycol/ethanol 7:3 (v/v)) was applied directly to both sides of the animal (~1.5×3 cm) using a Hamilton syringe. Two hours after oleic acid treatment, the TEWL rates of both sides were measured, and the RHS was treated with 30 µl of fluindostatin (1.5% fluindostatin in propylene glycol/ethanol 7:3 (v/v)) or TOFA (0.25% TOFA in propylene glycol/ethanol 7:3 (v/v)). TEWL was measured thereafter every 2 or 3 hours.

Figure 6A:
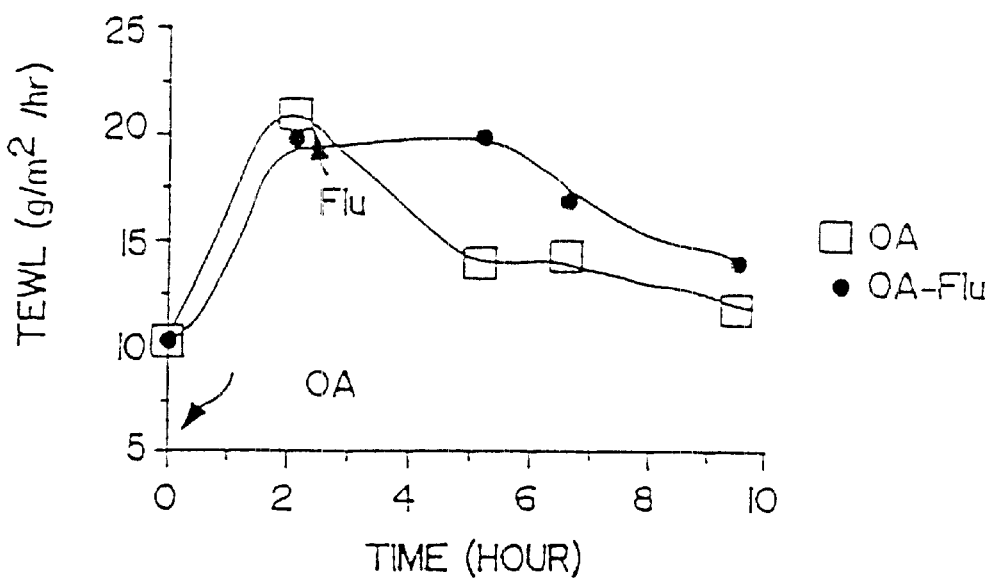
FIG. 6A shows TEWL when animals were treated with oleic acid followed by fluindostatin.
Figure 6B:
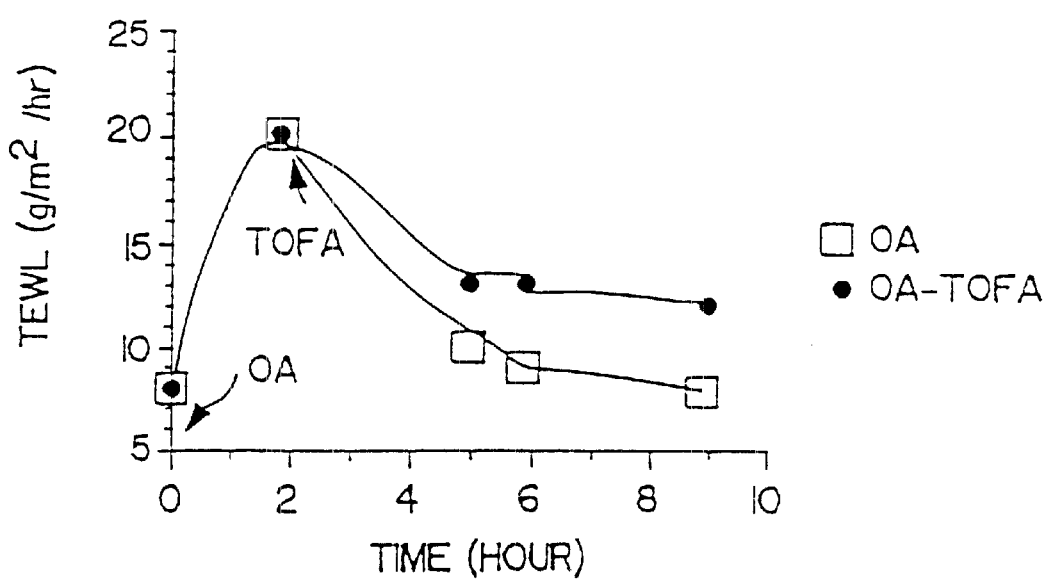
FIG. 6B shows TEWL when animals were treated with oleic acid followed by 5-(tetradecyloxy)-2-furoic acid (TOFA).

Test results are shown in FIGS. 6A and 6B. These data demonstrate that both fluindostatin and TOFA delay the recovery of the barrier, after prior barrier disruption by the oleic acid treatment.

EXAMPLE 7

TEWL (TRANS-EPIDERMAL WATER LOSS) CORRELATION WITH DRUG DELIVERY

To prove that disruption of the stratum corneum permeability barrier by this invention results in successful delivery of known pharmacologically active compounds the plasma and total body concentrations of lidocaine and luteinizing hormone releasing hormone (LHRH) after topical application, since all pharmaceuticals do not have the same physicol chemical characteristics of these two tested compounds, TEWL was measured also using the following protocol.

Four hairless mice were anesthetized with chloral hydrate as described in Example 6 and treated with acetone to disrupt the lipid barrier until the desired TEWL level was attained as monitored by a electrolytic water analyzer (Meeco Inc., Warrington, Pa.). The mice were kept under anesthesia until the harvest of tissue samples and then sacrificed. At time zero, the tested drug delivery compound listed in Tables 2–7 below was applied to the whole treated flank of each mouse. After four hours TEWL was measured again and two drug formulations, one containing lidocaine and the other containing Luteinizing Hormone Releasing Hormone (LHRH) in a vehicle of 60% ethanol, 20% propylene glycol and 20% water. Residual formulation was removed from the skin surface with cotton balls three times and the cotton balls were put into vial #1. Five tape-strippings were conducted at the treated skin sites, and each tape was put into an individual vial numbered 2–6. At the same time, blood was drawn and stored under refrigeration. Urine was collected from the mice during the two hour drug application period and placed into vial #8.

After an additional two hours, the treated skin was cut off, the subcutaneous fat was removed, and the whole skin was placed into vial #7 to which 1 ml of tissue solubilizer was added, and the mixture was allowed to digest overnight at 55° C. The corpse was digested in 100 ml of saponification mix at 55° C. overnight.

For analysis, 10 ml of Scintisafe (30%) Scintillation media (Fisher Scientific, Fairlawn, N.J.) was added to vials 1–6, and 8. The blood samples were centrifuged, and an aliquot of 100–200 µl was placed into vial #9 and 10 ml of Scintisafe (30%) was added. Similar aliquots of the corpse digest were placed into vials #10 and #11. To vials #9, 10, and 11, 100 µl of 30% hydrogen peroxide was added to decolorize the contents for about two hours. Then 16 µl of Scintisafe (30%) and 150 µl of acetic acid were added and the mixture was let stand overnight. All vials were subjected to scintillation counting as described above.

By testing pairs of inhibitors or s, each from a different metabolic pathway, faster screening could be achieved. Individual compounds within successful pairs were then tested to confirm barrier disruption and increased drug delivery activity of the sole compound. Two compounds from each chemical class were tested. The inhibitors and metabolic pathways are listed in Table 1 below. The vehicle for these studies is an effective drug delivery agent in its own right comprising propylene glycol ethanol, and water. The vehicle parameters are: TEWL 266±22 (T=4 hours); plasma concentration 0.31±0.03%; total body concentration 13.13±0.83 (% dose/ml plasma); N=14.

A portion of the LHRH plasma concentration specimens have been analyzed with a radioimmunoassay (RIA) at Hazelton, Washington Laboratories, Vienna, Va. to determine if successful transdermal delivery of this peptide occurred with Cellegy's drug delivery technology. Unfortunately, the LHRH RIA is a new test that seems to have a relatively higher amount of errors than more established RIA for other pharmacologically active compounds. The LHRH uptakes are listed in Table 8. The numbers reflect the ratio of the plasma levels following application of the tested drug delivery compound(s) to the vehicle, which is a very good delivery system itself. The wide range of variability (indicated by SEM) in the results does not allow for establishment of p values.

TABLE 1

| Inhibitor | Code | Inhibited Enzyme | Critical Lipid Metabolic Pathway |
|---|---|---|---|
| 5-Tetradecyloxy-2-furan-carboxylic acid | TOFA | Acetyl CoA Carboxylase | Free Fatty Acid |
| Fluindostatin | FLU | HMG CoA Reductase | Cholesterol |
| Lovastatin | LOV | HMG CoA Reductase | " |
| Cholesterol sulfate | CS | HMG CoA Reductase | " |
| β-Chloroalanine | BCA | Serine Palmitoyl Transferase | Ceramide |
| L-Cycloserine | LCS | Serine Palmitoyl Transferase | " |
| Fumonisin $B_1$ | FUM | Ceramide Synthetase | " |
| 1-Hexadecyl-3-trifluoro-ethyl glycero-sn-2-phosphomenthol | MJ33 | Phospholipase $A_2$ | Free Fatty Acid, Ceramide |
| Bromophenacylbromide | BPB | " | Free Fatty Acid, Ceramide |
| Conduritol-β-epoxide | CBE | Beta-glucocerebrosidase | Ceramide |
| Deoxynojirimycin | DOJ | Beta-glucocerebrosidase | " |
| Desipramine | DIN | Sphingomyelinase | " |
| N-Palmitoyl-DL-dihydroxysphingosine | PDHS | " | " |
| N-Oleoylethanolamine | NOEA | Ceramidase, Phospholipase $A_2$ | Ceramide, Free Fatty Acid |
| 4-Methylumbelliferyl-β-o-xyloside | MBX | Glucosyltransferase | Ceramide Degradation |
| Acid lipase | ALP | Degradation | Acylceramide Degradation |
| 1-Phenyl-2-decanoylamino-3-morpholino-1-propanol | PDMP | Glucosyltransferase | Ceramide Degradation |
| Mevastatin | MEV | HMG CoA Reductase | Cholesterol |
| 2-[n-morpholino]ethane-sulfonic acid | MES | Buffer | All |

TABLE 1-continued

| Inhibitor | Code | Inhibited Enzyme | Critical Lipid Metabolic Pathway |
|---|---|---|---|
| Chloroquine | CQ | Phospholipase $A_2$ Fatty Acid Synthetase, Ceramide Synthetase | Ceramide Free Fatty Acid |
| Gramicidin D | GD | Fatty Acid and Ceramide Synthetase | Ceramide Free Fatty Acid |
| Nicardipine | NIC | Phospholipase $A_2$ | Ceramide Free Fatty Acid |
| Cholesterol Oleate | CHO | HMG CoA Reductase | Cholesterol |

EXAMPLE 8

Studies were conducted using the same protocols as in Example 7 to inhibit rate-limiting synthetic enzymes for the three lipids that are critical for str atum comeum barrier function—free fatty acid, ceramide, and cholesterol. Inhibition disrupts the critical mole ratio of 1:1:1 thereby perturbing barrier function. Acetyl CoA Carboxylase (ACC) is the rate-limiting synthetic enzyme for free fatty acids, and its only known inhibitor is 5-tetradecyloxy-2-furancarboxyic acid (TO FA). Serine palmitoyl transferase (SPT) is the rate-limiting synthetic enzyme for ceramide, and its chemically unrelated inhibitors betachloroatanine and L-cycloserine were evaluated. 3-hydroxy-3-methylglutaryl (HMG) CoA Reductase is the rate-limiting synthetic enzyme for cholesterol and is inhibited. by three compounds that were tested—fluindostatin and lovastatin, which are chemically related, and cholesterol sulfate.

When the seven combinations of any two of these inhibitors of the critical lipid rate-limiting enzymes were applied together, they produced a statistically very significant ($p \leq 0.001$) increased delivery of lidocaine. Five combinations very significantly increased stratum corneum water permeabilities measured by TEWL and shown in Table 2. The TOFA combined with lovastatin or L-cycloserine produced a statistically significant increased water permeability, ($p=0.002-0.05$). TOFA combined with betachloroalanine produced the greatest delivery of lidocaine in this assay by increasing the drug's delivery by eight fold over vehicle control.

The TOFA and lovastatin combination successfully delivered the peptide LHRH transdermally as evidenced by plasma levels being 1.9 times higher than the amount of vehicle delivered as shown in Table 8.

EXAMPLE 9

Using the same protocol as in Example 8, the critical lipid rate-limiting enzyme inhibitors were tested as solitary agents as shown in Table 3. TOFA, fluindostatin, and cholesterol sulfate as the solitary inhibitors each produced a statistically very significant increase in lidocaine delivery while beta chloroalanine produced a significant increase. TOFA very significantly increased water permeability while fluindostatin and cholesterol sulfate significantly increased it. Beta chloroalanine did not increase stratum corneum water permeability in this assay.

EXAMPLE 10

In this study, the same protocols as used in Example 9 above were employed to test the effect upon transdermal delivery of lidocaine and LHRH by a combination of a rate-limiting enzyme inhibitor used in Example 9 with a nonrate-limiting synthetic enzyme of another of the three critical lipids. As shown in Table 4 below, all seven of these combinations successfully delivered lidocaine, with five producing a very significant increase. Fumonisin B1 combined with TOFA or fluindostatin, significantly increased lidocaine delivery.

Conduritol B epoxide, an inhibitor of βglucocerebrosidase, applied with fluindostatin very significantly increased stratum corneum water permeability but when combined with TOFA a significant increase in water permeability resulted.

Fumonisin B1, an inhibitor of ceramide synthetase, when combined with cholesterol sulfate, very significantly increased water permeability. When fumonisin B1 was applied with TOFA a significant increase of water permeability resulted.

When N-palmitayl-DL-dihydroxysphingosine (NPHS), an inhibitor of sphingomyelinase, was combined with fluindostatin, water permeability was significantly increased.

TOFA combined with N-palmitoyl-DL-dihydroxysphingosine (NPHS) successfully delivered transdermally the peptide LHRH to a level of 6.9 times higher than the amount delivered by the vehicle as shown in Table 8.

EXAMPLE 11

When two nonrate-limiting enzymes from different critical lipid biosynthetic pathways are combined, statistically very significant increased delivery of lidocaine occurs, as shown in Table 5. Seven of the eight tested combinations produced very significant or significant increases in stratum corneum water permeability also.

Inhibitors of phospholipase A such as bromophenacylbromide (BPB) and MJ33 are particularly active because they actually inhibit both free fatty acid and ceramide synthesis. All eight of the tested combinations comprise one of these two inhibitors. BPB combined with conduritol B epoxide, each at low concentration, produced a statistically significant increase in water permeability and a nearly significant ($p=0.05-0.10$) increase in lidocaine delivery. When the concentrations of these two inhibitors were increased by 5 and 4 fold respectively, water permeability and lidocaine delivery were both very significantly increased. When bromophenacylbromide is applied with desipramine, a sphingomyelinase inhibitor, a very significant increase of lidocaine and water permeability occurred at low concentration, but when desipramine was doubled only lidocaine delivery was very significant. This data suggests a dose response curve occurs with this invention and that the active agents do not act as non-specific destructive agents to the barrier.

When fumonisin B1 is applied with either BPB or MJ33, a very significant increase in lidocaine delivery, with a significant increase in water permeability occurs. When BPB is applied with deoxynojirimycin, an inhibitor of B glucocerebrosidase, or NPHS, very significant increases of lidocaine delivery and water permeability resulted.

BPB combined with NPHS most successfully delivered LHRH by increasing this peptide's delivery by 7.6 times greater than the amount delivered by the vehicle as shown in Table 8. BPB combined with deoxynojirimycin, and the combination of fumonisin B1 and MJ33 each increased delivery of LHRH by 2.0 and 1.7 times respectively as compared to vehicle.

Therefore, deficiency of free fatty acid and ceramide disrupts the critical lipid ratio, thereby perturbing the stratum corneum barrier and allowing increased drug delivery and water permeability.

EXAMPLE 12

When the non rate limiting enzyme inhibitors were used as solitary agents, usually the results were favorable, as shown in Table 6. The importance of inhibitor concentration as mentioned in Example 11 above is shown by conduritol B epoxide alone at a single application failing even nearly significantly to increase either water permeability or lidocaine delivery, even when the skin was prepermeabilized with acetone. Yet when it was frequently applied, even to intact skin, statistically significant increased lidocaine delivery and water permeability resulted.

The importance of intact skin application compared to prepermeabilized skin is demonstrated by the tested results of BPS. As a solitary agent, it nearly significantly increased lidocaine delivery, but not water permeability. But when applied to prepermeabilized skin, very significant increases of both lidocaine delivery and water permeability resulted.

Fumonisin B1 and N-oleoylethanolamine, an inhibitor of both phospholidase A and ceranidase, each very significantly increased lidocaine delivery while NPHS significantly increased it. Both NPHS and N-oleoylethanolamine very significantly increased water permeability. Fumonisin B1 successfully delivered LHRH as shown in Table 8 by increasing its delivery by 3.8 times greater than the vehicles.

EXAMPLE 13

The critical mole ratio of the three lipids in the stratum corneum barrier is also disrupted if normal degradation does not occur due to metabolic enzyme inhibition resulting in critical lipid accumulation as shown in Table 7. This concept was proven When lidocaine was successfully delivered and water permeability increased when ceramide metabolic pathways were blocked, resulting in its accumulation. The combination of N-oleoylethanolamine, with either PDMP or 4-methylumbelliferyl-B-O-xyloside, both inhibitors of glucosyl transferase, produced a statistically very significant increase in lidocaine delivery. The latter combination also significantly increased water permeability.

Acid lipase, metabolizes acylceramide to ceramide. Its application also results in significantly increased lidocaine delivery and water permeability.

Acid lipase as a solitary delivery compound increased LHRH plasma concentration by 2.2 times as compared with its vehicle, Morpholinoethane Sulfonic Acid (MES), as shown in Table 8.

TABLE 2

| Compounds | N | Conc (%) | TEWL (T = 4 hours) | P | Plasma Conc. (% dose/ml plasma) | P | Total Body Conc. (%) | P |
|---|---|---|---|---|---|---|---|---|
| TOFA + fluindostatin | 4 | 0.5/1.5 | 475 ± 34 | 0.001 | 0.78 ± 0.11 | <.001 | 35.62 ± 7.17 | <.001 |
| TOFA + cholesterol sulfate | 4 | 0.5/1.0 | 588 ± 54 | <.001 | 1.52 ± 0.35 | <.001 | 69.03 ± 1.68 | <.001 |
| TOFA + β-chloroalanine | 4 | 0.5/1.0 | 520 ± 1 | <.001 | 2.47 ± 0.22 | <.001 | 52.22 ± 3.90 | <.001 |
| TOFA + lovastatin | 4 | 0.5/2.5 | 440 ± 79 | 0.014 | 1.35 ± 0.34 | <.001 | 48.23 ± 7.87 | <.001 |
| β-chloroalanine + cholesterol sulfate | 4 | 1.0/1.0 | 525 ± 47 | <.001 | 0.68 ± 0.10 | <.001 | 37.28 ± 4.46 | <.001 |
| Fluindostatin + β-chloroalanine | 4 | 1.5/1.0 | 513 ± 41 | <.001 | 0.48 ± 0.06 | 0.018 | 25.75 ± 2.78 | <.001 |
| TOFA + L-cycloserine | 4 | 0.5/1.0 | 553 ± 56 | 0.021 | 1.32 ± 0.29 | <.0001 | 32.3 ± 3.17 | <.0001 |

TABLE 3

| Compounds | N | Conc (%) | TEWL (T = 4 hours) | P | Plasma Conc. (% dose/ml plasma) | P | Total Body Conc. (%) | P |
|---|---|---|---|---|---|---|---|---|
| TOFA | 4 | 1.0 | 520 ± 31 | <.001 | 1.20 ± 0.16 | <.001 | 39.69 ± 6.49 | <.001 |
| Fluindostatin | 4 | 1.5 | 431 ± 46 | 0.004 | 0.57 ± 0.19 | 0.133 | 23.69 ± 7.10 | 0.001 |
| β-chloroalanine | 4 | 1.0 | 263 ± 35 | 0.715 | 0.41 ± 0.08 | 0.242 | 19.04 ± 0.64 | 0.006 |
| cholesterol sulfate | 4 | 1.0 | 508 ± 169 | 0.040 | 0.99 ± 0.41 | 0.005 | 41.41 ± 7.73 | <.001 |

TABLE 4

| Compounds | N | Conc (%) | TEWL (T = 4 hours) | P | Plasma Conc. (% dose/ml plasma) | P | Total Body Conc. (%) | P |
|---|---|---|---|---|---|---|---|---|
| conduritol-β-epoxide + fluindostatin | 4 | 0.5/1.5 | 583 ± 128 | 0.001 | 0.84 ± 0.17 | <.001 | 30.86 ± 6.06 | <.001 |
| conduritol-β-epoxide + TOFA | 4 | 2.0/0.5 | 448 ± 80 | 0.040 | 1.27 ± 0.44 | 0.001 | 42.44 ± 9.52 | <.001 |
| fumonisin $B_1$ + fluindostatin | 4 | 0.5/1.5 | 533 ± 235 | >.05 | 0.29 ± 0.09 | <.006 | 11.58 ± 2.44 | <.02 |
| fumonisin $B_1$ + TOFA | 4 | 0.5/0.5 | 613 ± 170 | <.012 | 0.33 ± 0.08 | <.003 | 10.02 ± 1.09 | >.05 |
| N-palmitoyl-DL-hydroxysphingosine + TOFA | 3 | 0.5/0.5 | 148 ± 75 | >.1 | 0.83 ± 0.25 | <.0001 | 56.58 ± 14.48 | <.0001 |
| N-palmitoyl-DL-hydroxysphingosine + fluindostatin | 4 | 0.5/1.5 | 650 ± 68 | <.003 | 0.29 ± 0.04 | <.0001 | 18.67 ± 1.38 | <.0001 |
| fumonisin $B_1$ + cholesterol sulfate | 3 | 0.5/1.0 | 950 ± 43 | <.0001 | 0.52 ± 0.03 | <.0001 | 27.57 ± 6.93 | <.001 |

TABLE 5

| Compounds | N | Conc (%) | TEWL (T = 4 hours) | P | Plasma Conc. (% dose/ml plasma) | P | Total Body Conc. (%) | P |
|---|---|---|---|---|---|---|---|---|
| conduritol-β-epoxide + bromophenacylbromide | 4 | 0.5/0.05 | 398 ± 23 | 0.017 | 0.31 ± 0.04 | 0.968 | 16.73 ± 1.91 | 0.068 |
| conduritol-β-epoxide + bromophenacylbromide | 3 | 2.0/0.25 | 753 ± 149 | <.001 | 1.60 ± 0.42 | <.001 | 52.09 ± 6.28 | <.001 |
| desipramine + bromophenacylbromide | 4 | 0.5/0.1 | 595 ± 89 | <.001 | 0.64 ± 0.09 | <.001 | 22.26 ± 3.99 | 0.002 |
| desipramine + bromophenacylbromide | 4 | 1.0/0.1 | 365 ± 113 | 0.233 | 0.43 ± 0.04 | <.001 | 23.46 ± 1.69 | <.001 |
| fumonisin $B_1$ + bromophenacylbromide | 4 | 0.5/0.15 | 710 ± 196 | <.003 | 0.5 ± 0.16 | <.0001 | 20.41 ± 5.11 | <.0001 |
| fumonisin $B_1$ + MJ33 | 3 | 0.5/1.5 | 573 ± 101 | 0.016 | 0.4 ± 0.03 | <.0001 | 19.75 ± 0.83 | <.0001 |
| N-palmitoyl-DL-hydroxysphingosine + bromophenacylbromide | 4 | 0.5/0.1 | 1000 ± 0 | <.0001 | 0.47 ± 0.07 | <.0001 | 33.24 ± 2.07 | <.0001 |
| bromophenacylbromide + deoxynojirimycin | 4 | 0.2/4.0 | 753 ± 153 | <.001 | 0.65 ± 0.11 | <.001 | 34.60 ± 3.27 | <.001 |

TABLE 6

| Compounds | N | Conc (%) | TEWL (T = 4 hours) | P | Plasma Conc. (% dose/ml plasma) | P | Total Body Conc. (%) | P |
|---|---|---|---|---|---|---|---|---|
| conduritol-β-epoxide (intact skin) – TID, total 7–8 doses | 3 | 4.0 | 184 ± 39 | 0.008 | 0.82 ± 0.22 | 0.010 | 41.18 ± 10.69 | 0.010 |
| conduritol-β-epoxide | 4 | 4.0 | 253 ± 33 | 0.518 | 0.30 ± 0.04 | 0.809 | 15.70 ± 2.07 | 0.192 |
| fumonisin $B_1$ | 3 | 0.5 | 440 ± 149 | >.1 | 0.24 ± 0.03 | <.003 | 14.58 ± 0.73 | <.0001 |
| N-palmitoyl-DL-hydroxysphingosine | 4 | 0.5 | 793 ± 124 | <.0001 | 0.21 ± 0.03 | 0.012 | 6.88 ± 0.69 | >.1 |
| N-oleoylethanolamine | 4 | 0.5 | 720 ± 229 | <.001 | 1.2 ± 0.32 | <.0001 | 42.58 ± 2.4 | <.0001 |
| bromophenacylbromide (intact skin) | 3 | 0.15 | 98 ± 47 | 0.127 | 0.19 ± 0.10 | 0.165 | 14.73 ± 5.86 | 0.092 |
| bromophenacylbromide | 4 | 0.2 | 690 ± 177 | <.001 | 0.84 ± 0.07 | <.001 | 39.42 ± 11.09 | <.001 |

TABLE 7

| Compounds | N | Conc (%) | TEWL (T = 4 hours) | P | Plasma Conc. (% dose/ml plasma) | P | Total Body Conc. (%) | P |
|---|---|---|---|---|---|---|---|---|
| N-oleoylethanolamine + PDMP | 4 | 0.5/0.1 | 368 ± 47 | >0.1 | 0.9 ± 0.19 | <.0001 | 41.77 ± 3.27 | <.0001 |
| N-oleoylethanolamine + 4-methylumbelliferyl-β-o-xyloside | 4 | 0.5/1.0 | 525 ± 103 | 0.015 | 0.67 ± 0.06 | <.0001 | 55.39 ± 9.44 | <.0001 |
| Acid lipase in MES pH 5.5 - tape stripping | 4 | 1.0/20 mM | 385 ± 32 | 0.002 | 0.75 ± 0.05 | 0.748 | 45.90 ± 4.47 | 0.027 |

TABLE 8

| Compounds | Example | LHRH Delivery Ratio vs. Vehicle | SEM |
|---|---|---|---|
| TOFA + Lovastatin | 8 | 1.9 | 0.7 |
| TOFA + N-Palmitoyl-DL-dihydroxysphingosine | 10 | 6.9 | 4.3 |
| Bromophenacylbromide + N-Palmitoyl-DL-dihydroxysphingosine | 11 | 7.6 | 1.5 |
| Bromophenacylbromide + Deoxynojirimycin | 11 | 2.0 | 0.1 |
| Fumonisin $B_1$ + MJ33 | 11 | 1.7 | 0.9 |
| Fumonisin $B_1$ | 12 | 3.8 | 2.9 |
| Acid Lipase | 13 | 2.2 | 1.1 |

EXAMPLE 14

Three in vivo assays of intact pig skin were conducted using the active components of a commercially available testosterone patch as one control, the patch contained slightly less than 2.0% testosterone by volume [Androderm™, Theratech, Salt Lake, Utah].

The-penetration enhancing compounds tested at various concentrations were gramicidin D, choloroquine, and nicardipine, which inhibit ceramide and free fatty acid synthesis, and cholesterol oleate and mevastatin, which inhibit cholesterol synthesis. Test formulations (at room temperature) were applied sequentially to the test pig under occluded conditions using a Hilltop chamber (Hilltop Research, Miamiville, Ohio). The filter discs inside the chambers were saturated with 200 μl of the test formulation before application to the skin, except that any test gel was placed directly into the Hilltop chamber). Four pigs were used for each test compound in each assay.

The backs of four pigs were carefully clipped 24 hours prior to each of the three experiments. Each pig received 12 treatment sites and two control sites. One control site was untreated except that it was occluded by a cellophane patch secured by tape. The other control site received the testosterone (TS) alone. The sites were located randomly along the back and clearly demarcated with skin markers. A Tewameter™ TM 210 meter (Courage & Khazaki Electronic, Cologne, Germany), which had been allowed to warm up for 15 minutes, was used to measure the TEWL scores. A TEWL score was measured at each of the 14 sites at time points 0, 6, 24, 48, 72, 78, 96 and 102 hours after application. of the test substance Additional doses of the test substance were administered after the test readings at time points 6, 24, and 48 hours. The pig was sedated with ketamine/xylazine and placed in a sling for each test reading. To take the reading, the test chamber was removed, the site was gently blotted, and the measurements were taken ten minutes after removal of the chamber with the chambers being removed from sequential sites at four minute intervals. To take a measurement, the meter was set to Standard Reading (T°, %RH, TEWL), the probe was positioned over the test site, the start button was pushed, and a period of two minutes was allowed to elapse for the reading to stabilize before the reading was taken. A single reading for temperature, relative humidity, and TEWL (±SD) was recorded for each site.

In addition to the TEWL readings, each site was visually scored using the Draize scoring system as disclosed in J. H. Draize, *Food Drug Cosmet Law J*. 10:722–32, 1955, which is incorporated herein by reference in its entirety. All sites were redosed at time points 30 and 54 hours after the initial treatment without sedating the pig. The visual scorings used the Draize scoring system to record the description of the skin lesion, for example, edema, irritation, wound formation, etc. If a severe irritation developed at a specific treatment site (a Draize score of 3–4 for edema; 3–4 for erythema; or similar to an SDS-induced skin lesion), the site was terminated, and allowed to heal naturally while continuing the measurements of the other treatment sites.

There were a total of 11 observation times for TEWL and Draize scoring for each of 14 sites per pig, providing a total of 616 data points for four pigs for each of the three experiments. The results of these assays are provided in Tables 9–11. The TEWL measurements shown in Tables 9 and 10 provide an indication of barrier integrity. Mevastatin (MEV) decreased barrier integrity to a substantial degree over that provided by either control (except at 72 hours with the lowest dosage). The correlation between concentration and TEWL increase assumed a bell-shaped curve. The corresponding decrease in barrier integrity of the stratum corneum caused by MEV is shown in Table 11 by the superior capacity of MEV to deliver testosterone (TS) over that of both controls.

As shown in Table 9, N-Oleoylethanolamine (NOE) also increases barrier permeability in a dose response manner and with the increase being significantly superior to that provided by either control (except at the earliest time point for the lowest concentration). The ability of cholesterol oleate (CHO) to increase barrier permeability was comparable to or superior to both controls.

In addition, chloroquine (CQ), nicardipine (NIC), and gramicidin D (GD) also increase barrier permeability to TS to a degree significantly superior to that provided by either control at all time points (Table 11). Both NIC and GD perform in a dose response manner at all time points even 30 hours (post) after removal of the drug delivery formulation.

TABLE 9

| Compound tested (Weight %) | 24 h TEWL (x baseline) | 48 h TEWL (x baseline) | 72 h TEWL (x baseline) |
|---|---|---|---|
| Occlusion control | 1.21 | 1.26 | 1.40 |
| TS control | 1.53 | 1.82 | 2.68 |
| 0.08 MEV | 1.75 | 2.39 | 3.72 |
| 0.12 MEV | 1.79 | 2.75 | 3.72 |
| 0.03 NOE | 1.46 | 2.25 | 3.15 |
| 0.10 NOE | 1.67 | 2.45 | 3.68 |
| 0.05 CHO | 1.53 | 2.16 | 2.71 |

CHO = cholesterol oleate
MEV = mevastatin
NOE = N-Oleoylethanolamine
h = hours after first administration

TABLE 10

| Compound tested (Weight %) | 24 h TEWL (x baseline) | 48 h TEWL (x baseline) | 72 h TEWL (x baseline) | 6 h Post TEWL (x baseline) |
|---|---|---|---|---|
| Occlusion Control | 1.17 ± 0.17 | 1.62 ± 0.36 | 1.25 ± 0.11 | 1.08 ± 0.14 |
| TS Control | 1.00 ± 0.21 | 1.55 ± 0.47 | 1.77 ± 0.57 | 1.02 ± 0.42 |
| 0.006 MEV | 1.55 ± 0.29 | 2.13 ± 0.38 | 1.75 ± 0.21 | 1.24 ± 0.29 |
| 0.10 MEV | 1.93 ± 0.58 | 3.77 ± 1.42 | 3.04 ± 0.86 | 2.25 ± 0.8 |
| 0.25 MEV | 1.47 ± 0.18 | 2.66 ± 1.00 | 2.43 ± 0.51 | 1.90 ± 0.28 |

MEV = mevastain
h = hours after first administration
h post = hours after removal of drug delivery formulation

TABLE 11

| Compound tested (Weight %) | 24 h TEWL (x baseline) | 48 h TEWL (x baseline) | 72 h TEWL (x baseline) | 30 h Post TEWL (x baseline) |
|---|---|---|---|---|
| Occlusion Control | 1.38 ± 0.28 | 1.52 ± 0.36 | 1.27 ± 0.34 | 1.11 ± 0.19 |
| TS Control | 1.80 ± 1.33 | 2.41 ± 1.01 | 2.44 ± 1.18 | 1.25 ± 0.42 |
| 0.75 NIC + 2.00 TS | 2.35 ± 0.68 | 3.35 ± 0.42 | 3.22 ± 0.72 | 1.48 ± 0.18 |
| 1.00 NIC + 15.30 TS | 3.72 ± 0.94 | 3.46 ± 0.85 | 3.36 ± 1.64 | 1.39 ± 0.33 |
| 0.30 GD + 2.00 TS | 2.50 ± 0.84 | 3.04 ± 0.70 | 3.21 ± 0.62 | 1.53 ± 0.14 |
| 1.00 GD + 15.30 TS | 3.76 ± 1.04 | 4.07 ± 0.84 | 3.62 ± 0.80 | 2.18 ± 0.14 |
| 0.10 MEV + 2.00 TS | 2.69 ± 0.90 | 3.45 ± 1.25 | 3.40 ± 1.29 | 1.72 ± 0.31 |
| 0.06 CQ + 2.00 TS | 2.86 ± 0.91 | 3.78 ± 1.42 | 3.76 ± 0.93 | 1.61 ± 0.43 |

NIC = nicardipine
TS = testosterone
GD = Gramicidin D
CQ = Chloroquine
h = hours after first administration
h post = hours after removal of drug delivery formulation It will be apparent to one of ordinary skill in the art that many changes and modifications can be made in the invention, now being fully described, without departing from the spirit or scope of the invention.

What is claimed is:

1. A topical composition comprising an agent selected from the group consisting of inhibitors of ceramide synthesis, acylceramide synthesis, glucosylceramide synthesis, sphingomyelin synthesis, fatty acid synthesis, and cholesterol synthesis; inhibitors of phospholipid, glycosphingolipid, acylceramide and sphingomyelin degradation; degradation enzymes of free fatty acid, ceramide, sphingomyelin, acylceramide, and glucosylceramides; and both inhibitors and stimulators of metabolic enzymes of free fatty acids, ceramide, and cholesterol, together with a pharmaceutically acceptable carrier, wherein the agent is present at a concentration of about 0.01% to about 5.0% by weight of said composition.

2. A topical composition according to claim 1 wherein the agent is an inhibitor of HMG CoA reductase.

3. A topical composition according to claim 2 wherein the inhibitor of HMG CoA reductase is a member selected from the group consisting of simvastatin, lovastatin, fluindostatin, pravastatin, mevastatin, cholesterol sulfate, cholesterol phosphate, and oxygenated sterols.

4. A topical composition according to claim 2 wherein the inhibitor of HMG CoA reductase is a member selected from the group consisting of simvastatin, lovastatin, fluindostatin, pravastatin, and mevastatin.

5. A topical composition according to claim 2 wherein the inhibitor of HMG CoA reductase is mevastatin.

6. A topical composition according to claim 2 wherein the inhibitor of HMG CoA reductase is an oxygenated sterol.

7. A topical composition according to claim 1 wherein the agent is a member selected from the group consisting of inhibitors of serine palmitoyl transferase, inhibitors of ceramide synthetase, inhibitors of sphingomyelinase, inhibitors of β-glucosidase, inhibitors of acid lipase, inhibitors of α-hydroxylation, inhibitors of N-acyl chain length elongation, inhibitors of ω-acyl transferases, inhibitors of glucosyl transferase, and inhibitors of phosphatidylcholine-ceramide phosphatidylcholine transferase.

8. A topical composition according to claim 1 wherein the agent is a member selected from the group consisting of β-chloroalanine, fluoropalmitate, and β-fluoroalanine.

9. A topical composition according to claim 1 wherein the agent is fumonisins.

10. A topical composition according to claim 1 wherein the agent is a member selected from the group consisting of tricyclodecan-9-yl-xanthogenate, ethylisopropylamiloride, N-palmitoyl-DL-dihydroxysphingosine, and methylenedioxybenzapine.

11. A topical composition according to claim 1 wherein the agent is a member selected from the group consisting of N-hexylglucosyl-sphingosine, bromoconduritol-β-epoxide, conduritol, cyclophellitol, conduritol-β-epoxide, and deoxynojirimycin.

12. A topical composition according to claim 1 wherein the agent is a member selected from the group consisting of boronic acid, phenylboronic acid, tetrahydrolipstatin, and esterasin.

13. A topical composition according to claim 1 wherein the agent is a member selected from the group consisting of 1-phenyl-2-decanolamino-3-morpholino-1-propanol and its analogs.

14. A topical composition according to claim 1 wherein the agent is a member selected from the group consisting of 1-phenyl-2-decanolarmine-3-morpholine-1-propanol, p-nitro-phenyl-α-xyloside, 4-methyl umbelliferyl-β-O-xyloside, and o- and p-nitrophenyl-β-O-xyloparanoside.

15. A topical composition according to claim 1 wherein the agent is a member selected from the group consisting of inhibitors of acetyl CoA carboxylase, inhibitors of fatty acid synthetase, and inhibitors of phospholipase.

16. A topical composition according to claim 1 wherein the agent is 5-tetradecyloxy-2-furancarboxylic acid.

17. A topical composition according to claim 1 wherein the agent is gomisin A.

18. A topical composition according to claim 1 wherein the agent is a member selected from the group consisting of 2-(p-amylcinnamyl) amino-4-chlorobenzoic acid, bromophenacylbromide, 7,7-dimethyl-5,8-eicosadienoic acid, dibutyryl-cyclic AMP, diaminoethoxylhexesterol, N-oleoylethanolamine, and N-(7-nitro-2,1,3-benzoxadiazol-4-yl) phosphatidylserine.

19. A topical composition according to claim 1 wherein the agent is a member selected from the group consisting of inhibitors of phospholipid degradation, glycosphingolipid degradation, acylceramide degradation, and sphingomyelin degradation.

20. A topical composition according to claim 1 wherein the agent is a member selected from the group consisting of bromoconduritol-β-epoxide, conduritol-β-epoxide, and cyclophellitol.

21. A topical composition according to claim 1 wherein the agent is a member selected from the group consisting of degradation enzymes of free fatty acid, ceramide, sphingomyelin, acylceramide, or glucosylceramide.

22. A topical composition according to claim 1 wherein the agent is a member selected from the group consisting of ceramidase, sphingomyelinase, acid lipase, and β-glucosidase.

23. A topical composition according to claim 1 wherein the agent is a member selected from the group consisting of inhibitors and stimulators of metabolic enzymes of free fatty acids, ceramide, and cholesterol.

* * * * *